United States Patent [19]

Lamy

[11] 4,096,908
[45] Jun. 27, 1978

[54] HEATING AND COOLING ENCLOSURE FOR A GAS CHROMATOGRAPHIC COLUMN

[75] Inventor: Henri Lamy, Morlaas, France

[73] Assignee: Elf Union, Paris, France

[21] Appl. No.: 750,998

[22] Filed: Dec. 15, 1976

[30] Foreign Application Priority Data

Dec. 17, 1975 France .................. 75 38735

[51] Int. Cl.² .............. B01D 15/08; G01N 31/08
[52] U.S. Cl. ................................ 165/64; 73/23.1;
165/108; 219/201; 219/300; 219/400
[58] Field of Search ............... 73/23.1; 165/27, 48,
165/61, 64, 108; 219/201, 300, 400

[56] References Cited

U.S. PATENT DOCUMENTS

| 3,290,482 | 12/1966 | Dodd et al. | 73/23.1 X |
| 3,403,545 | 10/1968 | Carter | 73/23.1 |
| 3,422,603 | 1/1969 | Redmond | 55/386 |
| 4,011,904 | 3/1977 | Hope et al. | 165/108 |

Primary Examiner—Gerald A. Michalsky
Attorney, Agent, or Firm—Sughrue, Rothwell, Mion, Zinn and Macpeak

[57] ABSTRACT

The enclosure comprises an insulating and demountable sealed box unit fitted with a closure lid and placed around a chromatographic column consisting of a metal tube of constant cross-section, said tube being arranged in the form of a helix and supplied with electric heating current which is cut-off for cooling purposes. The heating and cooling air is supplied through a coaxial injection pipe and nozzle, circulated axially through and then around the column within the box unit, then discharged through the bottom wall of a collector casing.

7 Claims, 1 Drawing Figure

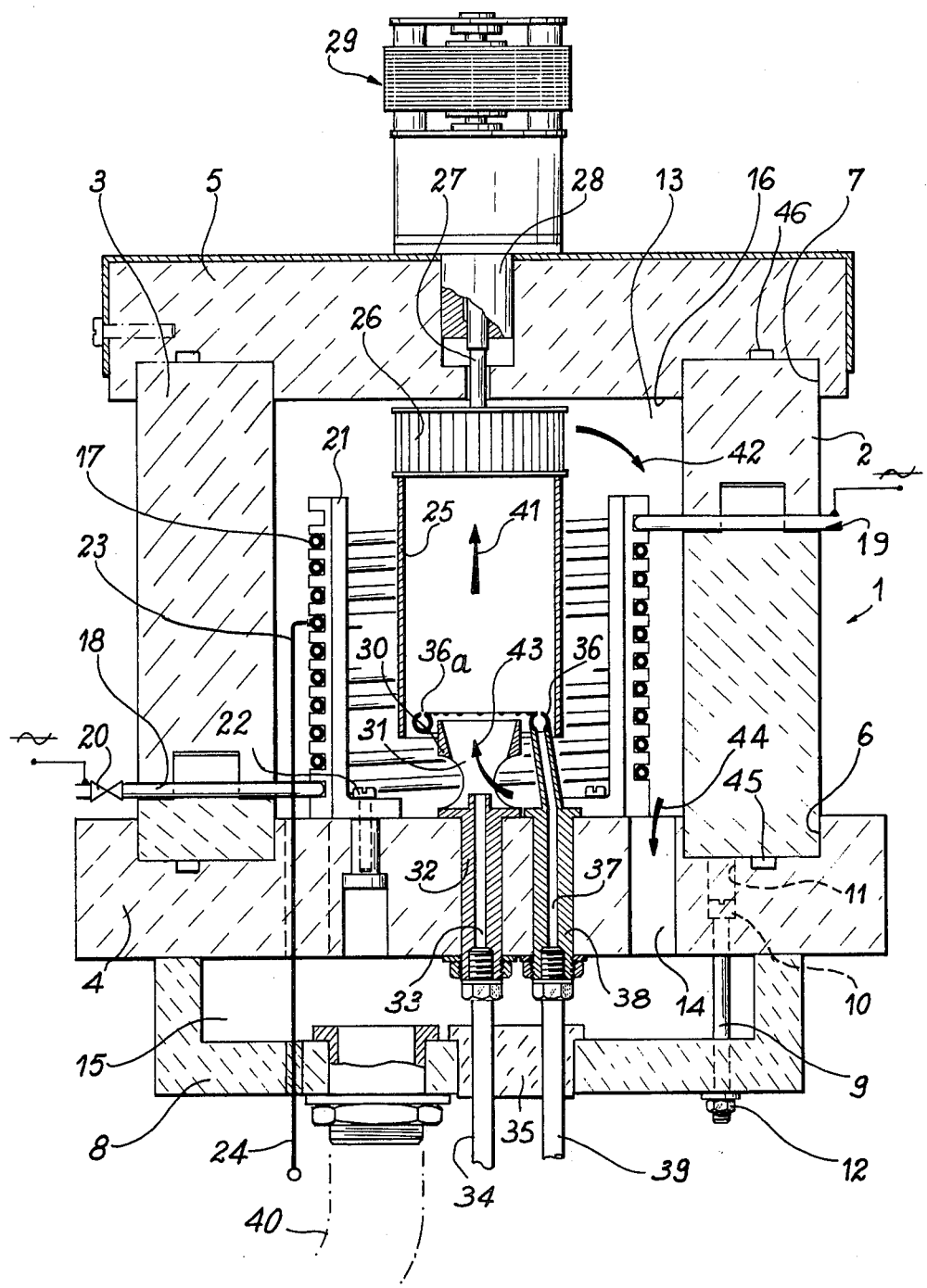

HEATING AND COOLING ENCLOSURE FOR A GAS CHROMATOGRAPHIC COLUMN

This invention relates to a heating and cooling enclosure for a gas chromatographic column which is primarily applicable to the analysis of pairs of petroleum products.

As is already known, there are a number of different designs of gas-phase chromatographic columns for carrying out automatic measurements not only in the laboratory but also in production units for industrial service. In these designs, the columns employed are usually constructed in the form of a tube having a constant cross-sectional area which is filled in particular with a product of small particle size having maximum permeability and constituting a support for the stationary phase or which is impregnated with this phase in its internal surface. Said tube is connected at one end to a valve for the introduction of a sample of the product to be examined and of an entrainment fluid or carrier fluid and at the other end to an inspection and measuring instrument of the type known as a flame ionization detector. The components of the sample which is injected into the column are separated from the stationary phase within this latter, then withdrawn from the column and transferred to the detector. This removal of components does not take place instantaneously but over a given elution period during which the concentration of each component varies so as to pass through a maximum value.

It is also known that, in order to obtain reproducible values of measurements and to improve the separation of the constituents of the product under inspection, it is necessary as a general rule to carry out the heating of the column either by maintaining this latter at a given stable temperature or preferably by operating the column in accordance with a temperature-rise program which is usually linear. This second solution which consists in increasing the temperature within the column as the components of the product are withdrawn therefrom permits the achievement of a balanced analysis in which good separation of the light components and rapid but sufficiently differentiated withdrawal of the heavy components are achieved at the same time.

It is an advantage to ensure that the above-mentioned temperature rise within the column and especially the programming of said temperature are carried out by means of direct heating of the column either by means of an external heat source in which the heat is transmitted to the tube by means of a fluid or solid heat exchanger or by causing said tube to perform the function of the secondary of a transformer or alternatively and preferentially by using the column itself as an electric resistance unit in which evolution of heat takes place by Joule effect under the action of the passage of a suitable electric current.

In point of fact, although devices of this type are well known in the technique, they usually suffer from the disadvantage of a response time which is still too long for continuous analysis of petroleum cuts. In fact, although the temperature rise can be carried out rapidly, the time of cooling of the column is usually of much longer duration. As a general result, the duration of the cycle is too long to permit utilization of the apparatus in such a manner as to be comparable to the continuous operation of conventional analyzers which are often less accurate but nevertheless preferred by reason of their speed of response.

The present invention relates to a heating enclosure for a chromatographic column which overcomes this disadvantage by means of an improved general technology resulting not only in a temperature rise which is programmed in accordance with a predetermined gradient but also in extremely rapid cooling at the end of each cycle of measurement.

To this end, the enclosure under consideration comprises an insulating and demountable box unit which surrounds the column and has a side wall which rests on a bottom support and is closed at the top by a lid, the column itself being constituted by a metallic tube having a constant cross-sectional area supplied with an electric heating current and wound in a helix having a vertical axis, and means for producing a circulation of air around the column within the box unit. The enclosure is distinguished by the fact that the means aforesaid comprise an open cylindrical skirt arranged coaxially within the interior of the column, a centrifugal fan placed in the axis and above the skirt so as to draw the air into said skirt and discharge the air into the spaces delimited on each side of the column between the skirt and the side wall of the insulating box unit, a nozzle also located in the axis of the column beneath the skirt, an air-injection pipe which opens into the throat of the nozzle and openings for the discharge of the injected air after circulation within the box unit in contact with the column, said openings being provided through the bottom support of the box unit.

In accordance with a particular feature, the tube of the column which is wound in a helix is supported in a fixed position at the center of the box unit by means of a plurality of insulating combs extending vertically and suitably arranged in spaced relation about the axis of the column.

Direct heating of the metallic tube of the column by means of an electric current of suitably adapted form and intensity makes it possible in known manner to produce a rapid and uniform temperature rise within the column. It is worthy of note that the column has a short response time in comparison with those obtained by other methods of heating and makes it possible to obtain a temperature gradient corresponding to any linear or other law by adapting the control of electric current passing through the tube to any suitable regulating device, the constructional detail of which has no direct bearing on the invention. In particular, the maximum slope of temperature rise is limited in the case of a column filled with a granular phase only by the rate of exchange between the tube and said phase. On the other hand and by virtue of the arrangements provided by the invention, the provision of means for circulating the environmental atmosphere around the column makes it possible not only during the stage of temperature rise to make this latter uniform at all points of the tube in a reliable and effective manner but above all during the cooling stage at the end of measurement to restore the enclosure to its initial thermal conditions within a particularly short period of time. By way of indication, the means in accordance with the invention readily permit the possibility of cooling from 350° C to 20° C over a period of time which is appreciably less than 4 minutes.

The technology adopted for constructing the enclosure in accordance with the invention is in fact primarily intended to improve the efficacy of the means mentioned above. To this end and in accordance with another distinctive feature, the internal surface of the insulating box unit is at least partially coated with a thin reflecting film especially of aluminum paper so as to ensure that the heat radiated by the tube of the column penetrates into the walls of said box to a depth which is as small as possible. The side wall, the bottom support and the top lid of the box unit are preferably formed by a material having an asbestos base and very low thermal conductivity, for example a material of the type known as "Marinite". Moreover, in order to limit outleakage from the box unit, the side wall is joined to the bottom support and the top lid by means of recesses providing leak-tight engagement and simple disassembly so as to permit of ready access to the column itself.

Cooling of the column is ensured by injection of air along the axis of the nozzle so as to impart velocity to said air which circulates first within the cylindrical skirt by reason of the sucking action of the centrifugal fan placed at the top portion of said skirt and is then discharged in contact with the column between the skirt and the side wall of the insulating box unit. Advantageously and in accordance with a further distinctive feature, the enclosure comprises an additional injection circuit for an auxiliary cooling fluid, said circuit being such as to comprise a ring pierced with holes surrounding the nozzle and supplied independently of this latter.

The air which is admitted into the insulating box unit for cooling the column is normally cooled through a heat exchanger by means of a refrigerating unit. This unit is preferably set at the temperature of the heat exchanger which is maintained under air pressure outside the stages of cooling of the enclosure.

In accordance with another distinctive feature, the enclosure comprises a thermocouple in which the sensitive portion is fixed on the surface of the tube of the column, preferably at a point located substantially at the mid-length of this latter. By means of a regulator and in accordance with a reference signal emitted by a programmer, said thermocouple makes it possible to control the value of the electric current which circulates within the column and consequently to produce action on the temperature rise within said column.

Further properties of a heating and cooling enclosure for a chromatographic column constructed in accordance with the invention will become apparent from the following description of one exemplified embodiment which is given by way of indication without any limitation being implied, reference being made to the single FIGURE of the accompanying drawing which is a diagrammatic transverse sectional view of an enclosure of this type.

In this FIGURE, the reference numeral 1 generally designates a heating and cooling enclosure in accordance with the invention. This enclosure mainly comprises an insulating box unit 2 having a side wall 3 which rests on a horizontal bottom support 4 and is closed at the top by a lid 5. The wall 3 formed of one or a number of juxtaposed elements is preferably engaged in recesses 6 and 7 respectively. Said recesses are in turn fitted with elastic seals 45 and 46 provided in the support and in the lid in order to limit points of direct outleakage. A collector casing 8 is added beneath the support 4 and secured against this latter by means of studs 9. The heads 10 of said studs are engaged in holes 11 formed in the support and the threaded ends of said studs cooperate with nuts 12 outside the casing 8. The box unit 2 as thus constituted delimits an internal region 13 which is suitably insulated from the external atmosphere. Said region 13 communicates with the internal space 15 of the casing 8 by means of a series of openings 14 suitably arranged in the bottom support 4. As an advantageous feature, provision is made on the internal surface of the insulating box unit, and especially on the side wall 3 of this latter and the top lid 5, for a lining which consists of a thin reflecting film 16 especially of aluminum paper or the like for reflecting the heat to the interior of the region 13 while preventing the heat from penetrating too deeply within the walls of the insulating box unit. These walls are preferably formed of material having very low heat conductivity, especially a substance having an asbestos base of the type known as "Marinite".

The region 13 which is delimited within the insulating box unit 2 is mainly occupied by a chromatographic column constituted by a metallic tube 17 having a constant cross-sectional area and suitably wound in a helix having a vertical axis. The ends 18 and 19 of said tube pass through the side wall 3 of the box unit 2 so as to be connected at one end to a valve 20 for introducing into said column a given fraction of a sample of a product to be examined and at the other end to a testing instrument of the type known as a flame ionization detector (not shown) for detecting the components of the sample progressively as these latter pass out of the column. The tube 17 is rigidly fixed in position within the box unit 2 and at the center of this latter by means of a series of supporting combs 21 spaced at intervals about the axis of the column and secured against the base support of the box unit by means of studs 22. Finally, a thermocouple 23 which is fixed against the external surface of the tube 17 substantially at the mid-point of its length records the temperature of the column and re-transmits said temperature through a conductor 24 to an external measuring and testing device for controlling the temperature rise of the column. To this end, said column is connected between the introduction valve and the measuring detector to a voltage source (also omitted from the drawing) in order to be supplied with an electric current for producing an evolution of heat by Joule effect within the metal of the tube itself.

In accordance with the invention, the column which is thus mounted within the insulating box unit 2 is associated with means for producing around said column a circulation of air which ensures during the stage of increase in temperature a uniform distribution of this latter within and around the column and also ensures during the cooling stage both efficient and rapid removal of the heat which has been generated.

To this end, the enclosure 1 comprises a cylindrical skirt 25 which is coaxial with the column 17 and mounted at the center of this latter; however, said column is placed nearer the side wall of the insulating box unit 2 than the external surface of the skirt 25. Said skirt is placed beneath the impeller wheel 26 of a centrifugal fan, the shaft 27 of which extends through a leak-tight passage 28 and is driven by a motor 29 mounted on the top wall of the box-unit lid 5. Moreover, the open bottom end of the skirt 25 is associated with a convergent-divergent nozzle 30; the throat 31 of said nozzle serves to impart velocity to the air which passes through the nozzle. The bottom support 4 of the box unit 2 is traversed at the level of said nozzle by a sleeve 32 having an axial bore 33, the extremity of which has its opening substantially at the level of the throat 31. Said bore 33 is joined at the opposite extremity to a supply pipe 34 which extends through a leak-tight bushing 35 fitted in the bottom wall of the collector casing 8. Finally, the nozzle 30 is surrounded by an auxiliary ring 36 pierced by a series of holes 36a in uniformly spaced relation. Said ring 36 is in turn connected by means of the internal bore 37 of a sleeve 38 which passes through the support 4 to a second supply pipe 39 for another cooling fluid under pressure which is intended to be admitted into the ring 36 in order to improve the cooling process. A duct 40 finally serves to remove the air and the fluid collected in the casing 8 after this latter has circulated within the region 13 of the enclosure and has passed through the openings 14.

The operation of the enclosure which has briefly been described in the foregoing takes place as follows. During the stage of heating in which the tube 17 of the column is supplied with electric current in accordance with a predetermined law, the temperature of the region 13 within the insulating box unit 2 is regularized and equalized at each point by the effect of agitation produced on the air surrounding the column by the combined action of the impeller wheel 26 of the centrifugal fan and of the nozzle 30, the circulation of hot air within the box unit being indicated schematically by the arrows 41, 42 and 43. On the other hand, during the cooling stage, the electric current within the tube 17 being cut-off, fresh air is immediately injected through the supply pipe 34 and the sleeve 32 along the axis of the nozzle 30 in order to be mixed with the hot air within the box unit and thus to ensure rapid cooling of this latter. The quantity of air thus injected is then removed in equal quantity in the direction indicated by the arrows 44 through the openings 14 provided in the bottom support 4 towards the casing 8 and the bushing 35. During cooling and especially when the temperature attains a predetermined and adjustable threshold value, an admission of auxiliary fluid such as cooled air or liquid nitrogen, for example, can be carried out by means of the ring 36, the nitrogen emerging from the hole 36a being mixed with the surrounding air in order to accelerate cooling to the initial temperature at which the cycle of measurement can be started again.

The heating and cooling enclosure for a chromatographic column which is thus provided is of simple design, the length of a cycle of measurement in said enclosure can be considerably limited whilst regulation of the admission of cooling fluids into the enclosure can readily be adjusted with respect to a predetermined threshold value as a function of the requirements of operation of the column. However, it is readily apparent that the invention is not limited to the single example of construction which has been more especially described with reference to the accompanying drawing but extends on the contrary to all alternative forms.

What we claim is:

1. A heating and cooling enclosure for a chromatographic column comprising an insulating and demountable box unit which surrounds the column and has a side wall which rests on a bottom support and is closed at the top by a lid, the column itself being constituted by a metallic tube having a constant cross-sectional area supplied with an electric heating current and wound in a helix having a vertical axis, and means for producing a circulation of air around the column within the box unit, wherein the means aforesaid comprise an open cylindrical skirt arranged coaxially within the interior of the column, a centrifugal fan placed in the axis and above the skirt so as to draw the air into said skirt and discharge the air into the spaces delimited on each side of the column between the skirt and the side wall of the insulating box unit, a nozzle also located in the axis of the column beneath the skirt, an air-injection pipe which opens into the throat of the nozzle and openings for the discharge of the injected air after circulation within the box unit in contact with the column, said openings being provided through the bottom support of said box unit.

2. An enclosure according to claim 1, wherein the column tube which is wound in a helix is supported in a fixed position at the center of the box unit by means of a plurality of insulating combs extending vertically and suitably arranged in spaced relation about the axis of the column.

3. An enclosure according to claim 1, wherein the internal surface of the insulating box unit is at least partially coated with a thin reflecting film formed especially of aluminum paper.

4. An enclosure according to claim 1, wherein the side wall, the bottom support and the top lid of the box unit are formed by means of a material having an asbestos base and very low thermal conductivity.

5. An enclosure according to claim 1, wherein the side wall of the box unit is joined to the bottom support and the top lid by means of recesses providing leaktight engagement.

6. An enclosure according to claim 1, wherein said enclosure comprises an additional injection circuit for an auxiliary cooling fluid, said circuit being such as to comprise a ring pierced with holes surrounding the nozzle and supplied independently of said nozzle.

7. An enclosure according to claim 1, wherein said enclosure comprises a thermocouple in which the sensitive portion is fixed on the surface of the tube of the column preferably at a point located substantially at the mid-length of said column.

* * * * *